(12) United States Patent
Chang et al.

(10) Patent No.: US 8,673,324 B2
(45) Date of Patent: Mar. 18, 2014

(54) METHOD FOR PRODUCING GAMMA-AMINOBUTYRIC ACID AND FOOD PRODUCED THEREBY

(75) Inventors: Ching-Hui Chang, Tainan (TW); Tsai-Mei Wu, Tainan (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 13/353,516

(22) Filed: Jan. 19, 2012

(65) Prior Publication Data

US 2013/0190400 A1    Jul. 25, 2013

(51) Int. Cl.
| | | |
|---|---|---|
| *A61K 9/00* | (2006.01) | |
| *A01N 65/00* | (2009.01) | |
| *A01N 63/02* | (2006.01) | |
| *A61K 35/00* | (2006.01) | |
| *A61K 8/66* | (2006.01) | |
| *A61K 8/96* | (2006.01) | |
| *A61Q 11/00* | (2006.01) | |

(52) U.S. Cl.
USPC ............. 424/400; 424/725; 424/780; 424/50

(58) Field of Classification Search
CPC .................. A23V 2002/00; A23V 2250/038; A23L 1/3018; A23L 1/3051; A61K 2800/85; A61K 8/44; A61K 8/97; A61K 8/99; A61Q 19/08; C12N 15/8214; C12N 15/8221; C12N 15/8243; C12N 15/8245; C12N 15/8247; C12N 15/825; C12N 15/8251
See application file for complete search history.

(56) References Cited

U.S. PATENT DOCUMENTS

| | | | |
|---|---|---|---|
| 5,854,057 A | 12/1998 | Ehret | |
| 6,582,939 B1 * | 6/2003 | Binder et al. | ................. 435/106 |
| 7,618,662 B2 | 11/2009 | Hines et al. | |
| 7,781,191 B2 | 8/2010 | Dunson, Jr. et al. | |
| 2004/0161524 A1 * | 8/2004 | Sakai et al. | ................. 426/655 |

FOREIGN PATENT DOCUMENTS

TW      200811293 A      3/2008

OTHER PUBLICATIONS

Takahashi, et al (Isolation and characterization of sake yeast mutants deficient in gamma-aminobutyric acid utilization in sake brewing, 2004, Journal of Bioscience and Bioengineering, vol. 97, pp. 412-418).*

Nirmaladevi et al (Analyses of the methanolic extract of the leaves of *Rhinacanthus nasutus*, Aug. 4, 2010, Journal of Medicinal Plants Research, vol. 4, pp. 1554-1560).*

Omni International Catalog, (Omni Ruptor 400 Ultrasonic Homogenizer, Effective Jan. 2006, p. 23 of 26).*

* cited by examiner

*Primary Examiner* — Brian-Yong Kwon
*Assistant Examiner* — Mark V Stevens
(74) *Attorney, Agent, or Firm* — Birch, Stewart, Kolasch & Birch, LLP

(57) ABSTRACT

The embodiment of invention provides a method for producing γ-aminobutyric acid, including the steps of providing a medium including *Saccharomyces cerevisiae*, adding an extract of *Rhinacanthus nasutus* into the medium and fermentating *Saccharomyces cerevisiae* in the medium added with the extract of *Rhinacanthus nasutus* to produce γ-aminobutyric acid.

12 Claims, 2 Drawing Sheets

METHOD FOR PRODUCING GAMMA-AMINOBUTYRIC ACID AND FOOD PRODUCED THEREBY

TECHNICAL FIELD

The technical field relates to the production of γ-aminobutyric acid and food produced thereby.

BACKGROUND

Gama-aminobutyric acid (γ-aminobutyric acid), also named GABA, is a nonproteinous amino acid, derived from glutamate and ornithine through metabolic pathways in living organisms. GABA is enriched in the vertebrate central nervous system, which is one of the mayor inhibitory neurotransmitters in the mammal central nervous system. The binding of GABA to the receptor $GABA_A$ on the neuron triggers the opening of the chloride ion selective pore to reduce the effect of excitatory neurotransmitters, resulting in inhibition on neurotransmission. In addition, the binding of GABA to the receptor $GABA_B$ triggers the opening of the potassium ion channel and presynaptic calcium ion channel to allow positively charged ions to move out from the neuron, resulting in inhibition on neurotransmission. Thus, GABA has a function which inhibits the overexcited central nervous system and stabilizes the brain. In clinical, GABA has been known for being used in the prevention or treatment of depression and insomnia and stabilizing blood pressure.

The well-known methods for producing GABA are based on biosyntheses. For instance, King H. K. et al provides a method for producing GABA by culturing Wilson's *Bacterium coli* Type I in a casein-hydrolysate glucose medium (King K. H. & Fletcher L. I., The Production of γ-Aminobutyric Acid by *Bacterium coli* Wilson, Type I, *Microbiology-sgm*, vol. 4, no. 2, p. 238-241, 1950). Recently, Guo X. F. et al has provided a method for producing GABA by a marine yeast isolate *Pichia anomala* MR-1 strain by using a solution containing monosodium glutamate and glucose and culturing at 40.5~48.0° C. (Guo X. F., et al., Optimal Reaction Conditions for Production of γ-Aminobutyric acid by the Marine Yeast Isolate *Pichia anomala* MR-1 Strain, *Biosci. Biotechnol. Biochem.*, 75(10), 1867-1871, 2011).

SUMMARY

One embodiment of the invention provides a method for producing γ-aminobutyric acid, comprising: providing a medium containing *Saccharomyces cerevisiae*, adding an extract of *Rhinacanthus nasutus* into the medium, and fermenting *Saccharomyces cerevisiae* in the medium containing of the extract of *Rhinacanthus nasutus* to produce γ-aminobutyric acid.

Another embodiment of the invention further provides a food comprising the fermented medium obtained from the said method.

DETAILED DESCRIPTION

Figure 1A:
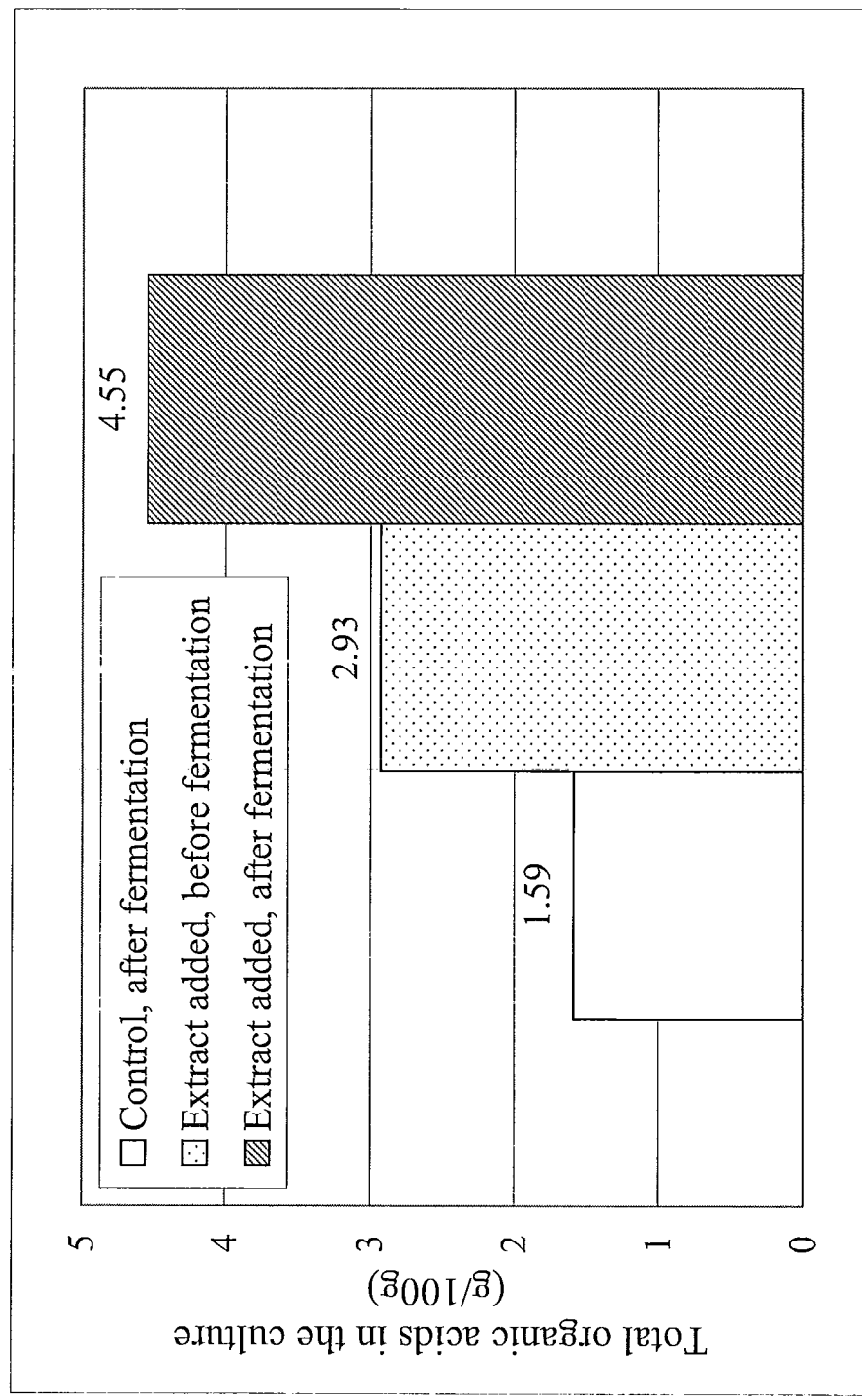
FIGS. 1A and 1B show the amounts of total organic acids and γ-aminobutyric acid in the culture with or without extracts of *Rhinacanthus nasutus* extracted with ultrasound vibration before or after fermentation in one example of the invention.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

According to one embodiment of the invention, the method for producing γ-aminobutyric acid is through yeast fermentation of *Saccharomyces cerevisiae* in a medium containing the extract of *Rhinacanthus nasutus*, resulting in a high yield of γ-aminobutyric acid.

The medium herein refers to a culture medium for *Saccharomyces cerevisiae* proliferation and fermentation. The medium can be any known media for *Saccharomyces cerevisiae* undergoing fermentation without specific limitations. For instance, the medium may comprise: sucrose, lactose, galactose, maltose or other sacchrides as the carbon source; peptone or other proteins as the nitrogen source; and ferrous sulfate ($FeSO_4.7H_2O$), potassium dihydrogen phosphate ($KH_2PO_4$), magnesium sulfate ($MgSO_4.7H_2O$) or other inorganic salts as the trace elements. The formulation of the medium may be suitably adjusted according to the fermentation conditions, such as temperature, times or the like.

One example of the invention uses a medium consisting of about 20~50 g/L of sucrose, about 5~20 g/L of lactose, about 5~20 g/L of maltose, about 0.01~0.5 g/L of ferrous sulfate ($FeSO_4.7H_2O$), about 0.1~2 g/L of potassium dihydrogen phosphate ($KH_2PO_4$) and about 0.1~5 g/L of magnesium sulfate ($MgSO_4.7H_2O$) for fermentation. In this example, the medium was autoclaved at 121° C. for 15~20 minutes in advance and then added the yeast *Saccharomyces cerevisiae*.

The *Saccharomyces cerevisiae* used in embodiment of the invention refers to a species of yeasts with an activity to enzymatically digest sugars into alcohols, which may be wild type or mutants and can be commercially available. The sugars that can be digested by *Saccharomyces cerevisiae* may comprise sucrose, fructose, lactose, glucose, maltose or other saccharides. The metabolic route of *Saccharomyces cerevisiae* enzymatically digesting sugars to generate acids, alcohols and carbon dioxide is called fermentation. According to the invention, the fermentation may last for 20~80 hours, or 72 hours, but may be suitably changed based on the fermentation conditions. The inoculation amount of *Saccharomyces cerevisiae* may also be adjusted according to the fermentation conditions. In one example of the invention, the inoculation amount of *Saccharomyces cerevisiae* was about 10%, which was about 5~20 g/L, relative to the total volume of the medium.

In the method according to one embodiment of the invention, the extract of *Rhinacanthus nasutus* is added into the fermentation medium. Through the fermentation process, the method of the invention is able to produce γ-aminobutyric acid efficiently with high yields.

The extract of *Rhinacanthus nasutus* according to one embodiment of the invention may be obtained from the following steps:

(i) providing a plant of *Rhinacanthus nasutus* or a part thereof, (ii) grinding the plant of *Rhinacanthus nasutus* or a part thereof and adding into water to form a first aqueous solution;

(iii) treating the first aqueous solution with heat or ultrasound vibration to obtain a second aqueous solution; and (iv) concentrating the second aqueous solution to obtain the extract of *Rhinacanthus nasutus*.

According one embodiment of to the invention, not only can the plant *Rhinacanthus nasutus* be extracted, but also parts of the plant can be extracted, such as its roots, stems, leaves, flowers, or other parts. The plant or plant part for extraction may be fresh without being processed or may be dried through a drying treatment. According to one embodiment of the invention, the fresh or dried plant or plant part is grinded and mixed with water to form the first aqueous solution. In one example, the ground plant or plant part relative to water has a weight ratio of about 1:10~1:20 (plant:water), or about 1:15~1:20, for the first aqueous solution. The first aqueous solution in one embodiment of the invention is then extracted with heat or ultrasound vibration under room temperature. The extraction with heat in one example refers to a process of putting the first aqueous solution in a heating container, raising the temperature of the container to 90~120° C. and keeping the temperature at that range for about 1 hour. The extraction with ultrasound vibration in one example refers to a process of putting the first aqueous solution in an ultrasound vibrator to vibrate at 15~30° C. for about 1~2 hours. The ultrasound vibration used in one embodiment of the invention is not specifically limited to a specific frequency. In one example, the frequency of the ultrasound vibration is about 10~22 KHz, and the output is about 110~150 W. According to one embodiment of the invention, the first aqueous solution being extracted with heat or ultrasound vibration refers to a second aqueous solution. The second aqueous solution can be further concentrated through filtration, vacuum drying, lyophilization or the like, to obtain the extract of *Rhinacanthus nasutus*.

According to one embodiment of the invention, it may add the extract of *Rhinacanthus nasutus* in the medium before *Saccharomyces cerevisiae* is added. The extract of *Rhinacanthus nasutus* may be added before the medium is autoclaved. In one example, the extract of *Rhinacanthus nasutus* is added in amount of about 0.25~1.5 g/L based on the total volume of the medium. According to the examples below, the γ-aminobutyric acid content in the medium containing the *Rhinacanthus nasutus* extract after fermentation was about four-folds that of before fermentation. Moreover, the γ-aminobutyric acid content in the medium containing the *Rhinacanthus nasutus* extract after fermentation was about 18-folds that of the medium without the extract. The results apparently showed that the method according to the invention was able to efficiently produce γ-aminobutyric acid with high yields.

Accordingly, another embodiment of the invention provides a food comprising the fermented medium obtained from the method above. According to one embodiment of the invention, the fermented medium can be directly eaten or drunk without filtration or concentration, but is not limited thereto. The fermented medium may be filtered or sterilized if necessary. The food according to one embodiment of the invention may alternatively be a functional beverage or additive added to a diet for the uptake of γ-aminobutyric acid.

Due to a high content of γ-aminobutyric acid, the food according to one embodiment of the invention can be health food or functional food for preventing or treating hypertension, depression, insomnia or the like. Furthermore, the food according to one embodiment of the invention may be mixed or eaten with other foods or drinks. The food according to one embodiment of the invention may further comprise additives, such as sweeteners, flavoring, pigments, thickeners, coagulates, antioxidants, or preservatives, for food processing.

EXAMPLE 1

Preparation of *Rhinacanthus nasutus* Extracts and Analyses of Components Thereof Fresh and dried leaves of *Rhinacanthus nasutus* 100 g were ground respectively. The ground leaves were added to water at a weight ratio of about 1:20 (leaves:water).

In one group, the aqueous solution containing the ground fresh/dried leaves were separately added into an electromagnetic heating stirrer (CORNING, PC420D) and extracted at 100° C. for 1 hour. The extracted solutions were respectively filtered. The filtrates were then lyophilized. Dark green powders were obtained with a yield of about 10~15%.

In another group, the aqueous solution containing the ground fresh/dried leaves were separately added into an ultrasound vibrator (SONICS&MATERIALS INC., VCX130) with a 20 KHz frequency and 130 W output and vibrated for 1 hour. The extracted solutions were respectively filtered. The filtrates were then lyophilized. Dark green powders were obtained with a yield of about 10~15%.

The extracts of the fresh or dried leaves with heating and ultrasound vibration were kept for the next step.

The extract of the fresh leaves extracted with ultrasound vibration was further analyzed under HPLC, showing about 17~25 mg/g of plant polyphenols, about 10~18 mg/g of total flavonoids, about 10~15 mg/g of gallic acid, about 3~6 ppm of rutin, about 2~3.5 ppm of chlorogenic acid and about 1.2~2.5 ppm of p-coumaric acid.

EXAMPLE 2

Medium Formulation and Culturing

Strain Activation

Powders of *Saccharomyces cerevisiae* purchased from Taiwan Bioresource Collection and Research Center (BCRC 20577) were inoculated into a 5 mL-YM broth (DIFCO). After 24 hours, the yeasts were moved to a YM plate (Agar, DIFCO) for another incubation period for 24 hours. The plate was then preserved in a 4° C. refrigerator.

Culturing

A single colony on the plate was picked off with a sterile loop and inoculated into a 5 mL-YM broth for static incubation at 34° C. for 24 hours. The broth was then pooled into a 400 mL-YM broth for another static incubation at 34° C. for 24 hours. The cultured broth was kept for the next step.

Medium Formulation

The formulation of the medium is listed in Table 1. The extracts of fresh or dried leaves extracted with heating or ultrasound vibration obtained from Example 1 were individually added into the medium to form a final concentration of 0.5%. Each medium was added with water to form 1-liter volume and then autoclaved (121° C., 15~20 min). A medium without adding any *Rhinacanthus nasutus* extracts was set as a control.

TABLE 1

Medium formulation

| Component | Concentration (g/L) |
|---|---|
| $MgSO_4 \cdot 7H_2O$ | 0.2 |
| $K_2HPO_4$ | 0.5 |
| $FeSO_4 \cdot 7H_2O$ | 0.04 |
| Sucrose | 30 |
| Lactose | 10 |
| Maltose | 10 |

10% (v/v) of the cultured broth was added to each autoclaved medium 300 mL and incubated at 25~37° C. for 70~74 hours with gentle shaking (50~150 rpm). The effects of the *Rhinacanthus nasutus* extracts on the yeasts growth were recorded. The yeasts growth was monitored through the pH value, the absorbance at wavelength of 660 nm (OD660), the biomass and the colony-forming units of the medium after fermentation. All results showed that the extracts were beneficial to the yeast growth.

Moreover, the content of the total organic acids before and after fermentation of the medium containing the fresh-leaves extract extracted with ultrasound vibration was analyzed according to the rule of CNS 12635 and the content of γ-aminobutyric acid before and after the fermentation of the medium containing the fresh-leaves extract extracted with ultrasound vibration was also analyzed by using ionic chromatography. The contents of the total organic acids and γ-aminobutyric acid after the fermentation of the medium without adding the *Rhinacanthus nasutus* extract was determined as a control. The results are shown in FIGS. 1A and 1B.

Figure 1B:
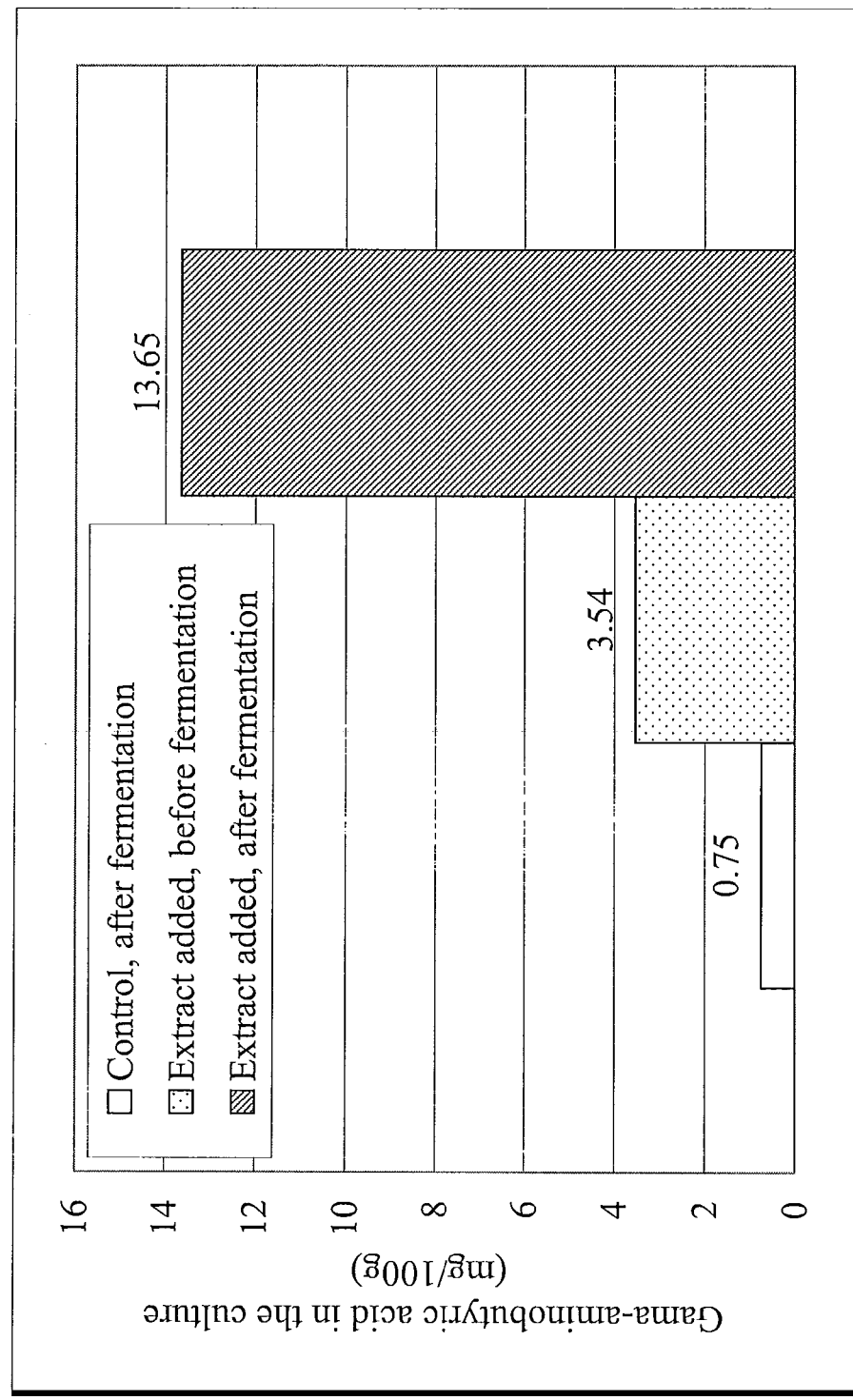

According to FIGS. 1A and 1B, the γ-aminobutyric acid content in the medium containing the *Rhinacanthus nasutus* extract after fermentation was about 4-folds that of before fermentation (13.65/3.54). In addition, the γ-aminobutyric acid content in the medium containing the *Rhinacanthus nasutus* extract after fermentation was about 18-folds that of the medium without adding the extract (13.65/0.75). According to the results, the yeast fermentation in a medium containing the *Rhinacanthus nasutus* extract was able to efficiently produce γ-aminobutyric acid (GABA).

It will be apparent to those skilled in the art that various modifications and variations can be made to the disclosed embodiments. It is intended that the specification and examples be considered as exemplary only, with a true scope of the disclosure being indicated by the following claims and their equivalents

What is claimed is:

1. A method for producing γ-aminobutyric acid, comprising:
   providing a medium containing *Saccharomyces cerevisiae*,
   adding an extract of *Rhinacanthus nasutus* into the medium, and
   fermenting *Saccharomyces cerevisiae* in the medium containing the extract of *Rhinacanthus nasutus* to produce γ-aminobutyric acid.

2. The method as claimed in claim 1, wherein the extract of *Rhinacanthus nasutus* is obtained from the following steps:
   (i) providing a plant of *Rhinacanthus nasutus* or a part thereof,
   (ii) grinding the plant of *Rhinacanthus nasutus* or a part thereof and adding into water to form a first aqueous solution;
   (iii) treating the first aqueous solution with heat or ultrasound vibration to obtain a second aqueous solution; and
   (iv) concentrating the second aqueous solution to obtain the extract of *Rhinacanthus nasutus*.

3. The method as claimed in claim 2, wherein the weight ratio of the ground plant or a part thereof relative to water in the step (ii) is about 1:10~1:20.

4. The method as claimed in claim 2, wherein the heat treatment in the step (iii) is in a range of about 90~120° C.

5. The method as claimed in claim 2, wherein the frequency of the ultrasound vibration in the step (iii) is in a range of about 18~22 KHz.

6. The method as claimed in claim 2, wherein the plant or a part thereof is fresh or dried.

7. The method as claimed in claim 1, wherein the medium is added with about 0.25~1.5 g/L of the extract of *Rhinacanthus nasutus* based on the total volume of the medium.

8. The method as claimed in claim 1, wherein the medium contains about 5~20 g/L of *Saccharomyces cerevisiae* based on the total volume of the medium.

9. The method as claimed in claim 1, wherein the medium further comprises about 20~50 g/L of sucrose, about 5~20 g/L of lactose, about 5~20 g/L of maltose, about 0.01~0.5 g/L of ferrous sulfate ($FeSO_4.7H_2O$), about 0.1~2 g/L of potassium dihydrogen phosphate ($KH_2PO_4$), and about 0.1~5 g/L of magnesium sulfate ($MgSO_4.7H_2O$).

10. The method as claimed in claim 1, wherein the fermentation lasts for about 20~80 hours.

11. A food comprising a fermented medium obtained from the method as claimed in claim 1.

12. The food as claimed in claim 11, used for preventing or treating hypertension, depression or insomnia.

* * * * *